(12) United States Patent
Watanabe et al.

(10) Patent No.: US 6,412,978 B1
(45) Date of Patent: Jul. 2, 2002

(54) X-RAY DIAGNOSTIC APPARATUS

(75) Inventors: Naoto Watanabe, Nasu-gun; Satoru Oishi, Otawara, both of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/476,082

(22) Filed: Jan. 3, 2000

(30) Foreign Application Priority Data

Jan. 11, 1999 (JP) .......................................... 11-004423

(51) Int. Cl.$^7$ ................................................. H05G 1/02
(52) U.S. Cl. ...................................... 378/197; 378/196
(58) Field of Search ................................ 378/197, 196, 378/198, 4

(56) References Cited

U.S. PATENT DOCUMENTS

| 5,493,597 | A | * | 2/1996 | Gotoh et al. | ............... | 378/98.2 |
| 5,680,434 | A | * | 10/1997 | Thelosen et al. | ........... | 378/150 |
| 6,129,668 | A | * | 10/2000 | Haynor et al. | .............. | 600/424 |
| 6,155,713 | A | * | 12/2000 | Watanabe | .................. | 378/197 |
| 6,200,024 | B1 | * | 3/2001 | Negrelli | ...................... | 378/197 |
| 6,222,544 | B1 | * | 4/2001 | Tarr et al. | .................... | 345/349 |
| 6,222,902 | B1 | * | 4/2001 | Lin et al. | ...................... | 378/22 |

* cited by examiner

*Primary Examiner*—Robert H. Kim
*Assistant Examiner*—Irakli Kiknadze
(74) *Attorney, Agent, or Firm*—Oblon, Spivak, McClelland, Maier & Neustadt, P.C.

(57) ABSTRACT

An X-ray diagnostic apparatus includes an X-ray tube for irradiating a subject with X-rays, a rectangular planar type X-ray detector formed by arraying a plurality of solid-state detection elements, a supporting mechanism for supporting the X-ray tube and the planar type X-ray detector in arbitrary postures with respect to the subject, and a suspending mechanism for suspending the planar type X-ray detector from the supporting mechanism. The suspending mechanism has a rotating mechanism for rotating the planar type X-ray detector through an arbitrary angle about a central path of the X-rays. When necessary, the planar type X-ray detector is rotated about the central path of the X-rays so as to be very close to the subject. When necessary, the planar type X-ray detector is rotated, so that the longitudinal direction of the subject on the image and the vertical direction of the screen can coincide with each other.

18 Claims, 13 Drawing Sheets

X-RAY DIAGNOSTIC APPARATUS

BACKGROUND OF THE INVENTION

The present invention relates to an x-ray diagnostic apparatus in which the imaging angle with respect to a subject has a high degree of freedom and which is suitable for inspecting a circulatory organ.

A conventional X-ray image diagnostic apparatus, particularly a circulatory organ X-ray image diagnostic apparatus that can be used during operation using a catheter or the like, is elaborated in various manners to ensure a sufficiently large operation space for the operator while increasing the degree of freedom of the imaging posture with respect to the subject. For example, a C arm is supported to be rotatable about three orthogonal rotating shafts and slidable along rails set on the ceiling or floor surface.

FIG. 1 is a perspective view of the gantry of a conventional X-ray diagnostic apparatus. An X-ray tube 150 and an X-ray detection system are supported by a C-shaped (or U-shaped) arm 152 to oppose each other through a bed 156. The arm 152 can slide along an arm holder 153 (arrow A). The arm holder 153 is tiltably held by a holder pillar 154 (arrow B). The holder pillar 154 is rotatably attached to a ceiling base 157 (arrow C). The ceiling base 157 can slide on the ceiling along rails (arrows D and E). These composite motions A to F increase the degree of freedom of the postures of the X-ray tube 150 and the X-ray detection system with respect to a subject P. The mainstream X-ray detection system is a combination of an image intensifier (I.I.) 151 and TV camera 155. A moving mechanism is provided to move the X-ray detection system close to/away from the subject P (arrow F). A o rotating mechanism is provided in order to mechanically rotate the TV camera 155 by an angle corresponding to a rotation C of the arm 152, so that the longitudinal direction of the subject P and the vertical direction of the display screen coincide with each other.

The I.I. 151 and TV camera 155 are heavy and large in size. Accordingly, the gantry becomes large in size. In recent years, a lightweight, compact planar type X-ray detector has been developed to replace the X-ray detection system comprised of the I.I. 151 and TV camera 155. This planar type X-ray detection system is comprised of a phosphor film and a solid-state detection element array arranged behind the phosphor film, converting optical signals into electrical signals. The system may be comprised of a solid-state detection element array directly converting X-ray signals into electrical signals. The solid-state detection element array is comprised of a plurality of photoelectric conversion elements, a plurality of charge storing diodes for storing charges generated by the photoelectric conversion elements, and a plurality of charge read field effect transistors (FETs). X-rays are converted into light by the phosphor film. Charges in an amount corresponding to the intensity of the light are generated by the photoelectric conversion elements. The charges are stored in the charge storing diodes and are read out as imaging signals through the FETs.

The closer the planar type X-ray detector is to the subject P, the higher the image quality. The planar type X-ray detector has a rectangular shape, and depending on its posture, its corner may abut against the subject P. In this case, the planar type X-ray detector cannot be moved further closer to the subject P.

BRIEF SUMMARY OF THE INVENTION

It is an object of the present invention to provide an X-ray diagnostic apparatus in which a planar type X-ray detector can be moved very close to the subject.

In order to achieve the above object, according to the present invention, there is provided an X-ray diagnostic apparatus comprising: an X-ray tube configured to irradiate a subject with X-rays; a rectangular planar type X-ray detector formed by arraying a plurality of solid-state detection elements; a supporting mechanism configured to support the X-ray tube and the planar type X-ray detector in arbitrary postures with respect to the subject; and a suspending mechanism configured to suspend the planar type X-ray detector from the supporting mechanism, the suspending mechanism having a rotating mechanism for rotating the planar type X-ray detector through an arbitrary angle about a central path of the X-rays. When necessary, the planar type X-ray detector can be rotated so as to be very close to the subject. When necessary, the planar type X-ray detector is rotated, so that the longitudinal direction of the subject on the image and the vertical direction of the screen can coincide with each other.

There is also provided an X-ray diagnostic apparatus comprising: an X-ray tube configured to irradiate a subject with X-rays; a rectangular planar type X-ray detector formed by arraying a plurality of solid-state detection elements; a supporting mechanism configured to support the X-ray tube and the planar type X-ray detector in arbitrary postures with respect to the subject; and a suspending mechanism configured to suspend the planar type X-ray detector from the supporting mechanism, the suspending mechanism having a tilt mechanism for tilting the planar type X-ray detector by an arbitrary angle about a central path of the X-rays. When necessary, the planar type X-ray detector can be tilted so as to be very close to the subject.

There is also provided an X-ray diagnostic apparatus comprising: an X-ray tube configured to irradiate a subject with X-rays; a rectangular planar type X-ray detector formed by arraying a plurality of solid-state detection elements; a supporting mechanism configured to support the X-ray tube and the planar type X-ray detector in arbitrary postures with respect to the subject; and a suspending mechanism configured to suspend the planar type X-ray detector from the supporting mechanism, the suspending mechanism having a mechanism for moving the planar type X-ray detector close to/away from the subject. When necessary, the planar type X-ray detector can be moved close to/away from the subject so as to be very close to the subject.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An X-ray diagnostic apparatus according to a preferred embodiment of the present invention will be described with reference to the accompanying drawings.

Figure 2:
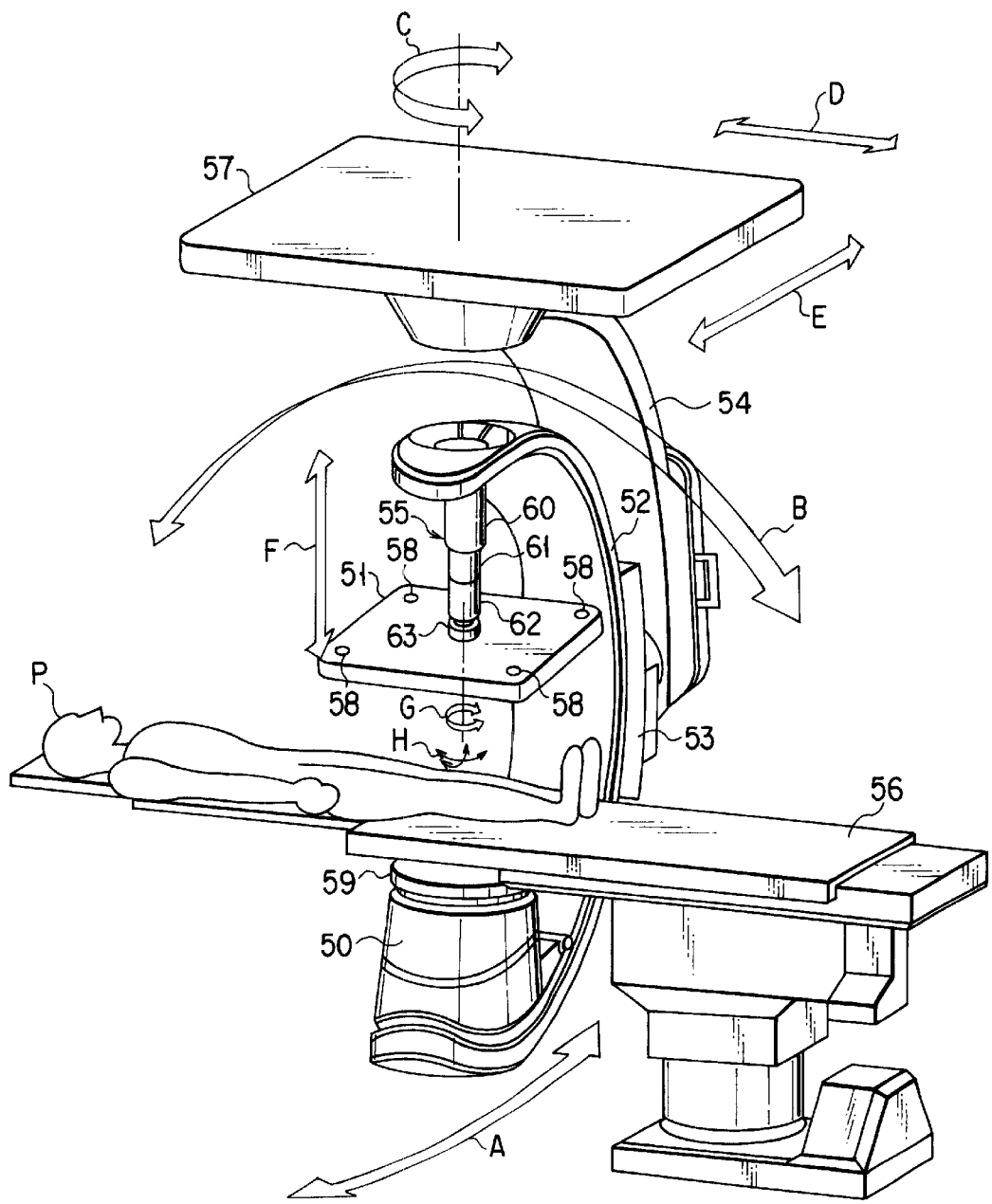
FIG. 2 is a perspective view of the gantry of a circulatory system X-ray diagnostic apparatus according to an embodiment of the present invention.

FIG. 2 is a perspective view of the gantry of an X-ray diagnostic apparatus according to an embodiment of the present invention. An X-ray tube 50 is mounted on the lower end of an arcuate arm 52. A collimator 59 having a variable-shape aperture is attached to the X-ray radiation window of the X-ray tube 50. The arcuate arm 52 is constructed of a C- or U-shaped member. In this embodiment, a description will be made for a C-shaped arm 52. A square or rectangular planar type X-ray detector 51 is supported on the upper end of the C-shaped arm 52 through a rod-like suspension mechanism 55. The planar type X-ray detector 51 opposes the X-ray tube 50 through a bed 56. The suspension mechanism 55 is connected to the center of the planar type X-ray detector 51.

The planar type X-ray detector 51 is comprised of a phosphor film for converting X-rays into light, and a plurality of solid-state detection elements arrayed on the rear surface of the phosphor film. Each solid-state detection element is comprised of a photoelectric conversion element for generating charges in an amount corresponding to the light intensity, a charge storing diode for storing the charges generated by the photoelectric conversion element, and a field effect transistor (FET) for reading the stored charges as an imaging signal.

A noncontact sensor 58 is attached to each of the four corners of the planar type X-ray detector 51. When either one of the four corners of the planar type X-ray detector 51 moves close to a subject P by a predetermined distance or more, that is, immediately before it comes into contact with the subject P, the corresponding noncontact sensor 58 senses this proximity movement. When the proximity movement is sensed, the motion of the planar type X-ray detector 51 is limited. This will be described later in detail.

The C-shaped arm 52 is supported by an arm holder 53 to be slidable along an arrow A. The arm holder 53 is supported by a holder pillar 54 to be tiltable along an arrow B. The holder pillar 54 is attached to a ceiling base 57 to be rotatable along an arrow C. The ceiling base 57 is attached to ceiling rails to be slidable along arrows D and E.

Figure 1:
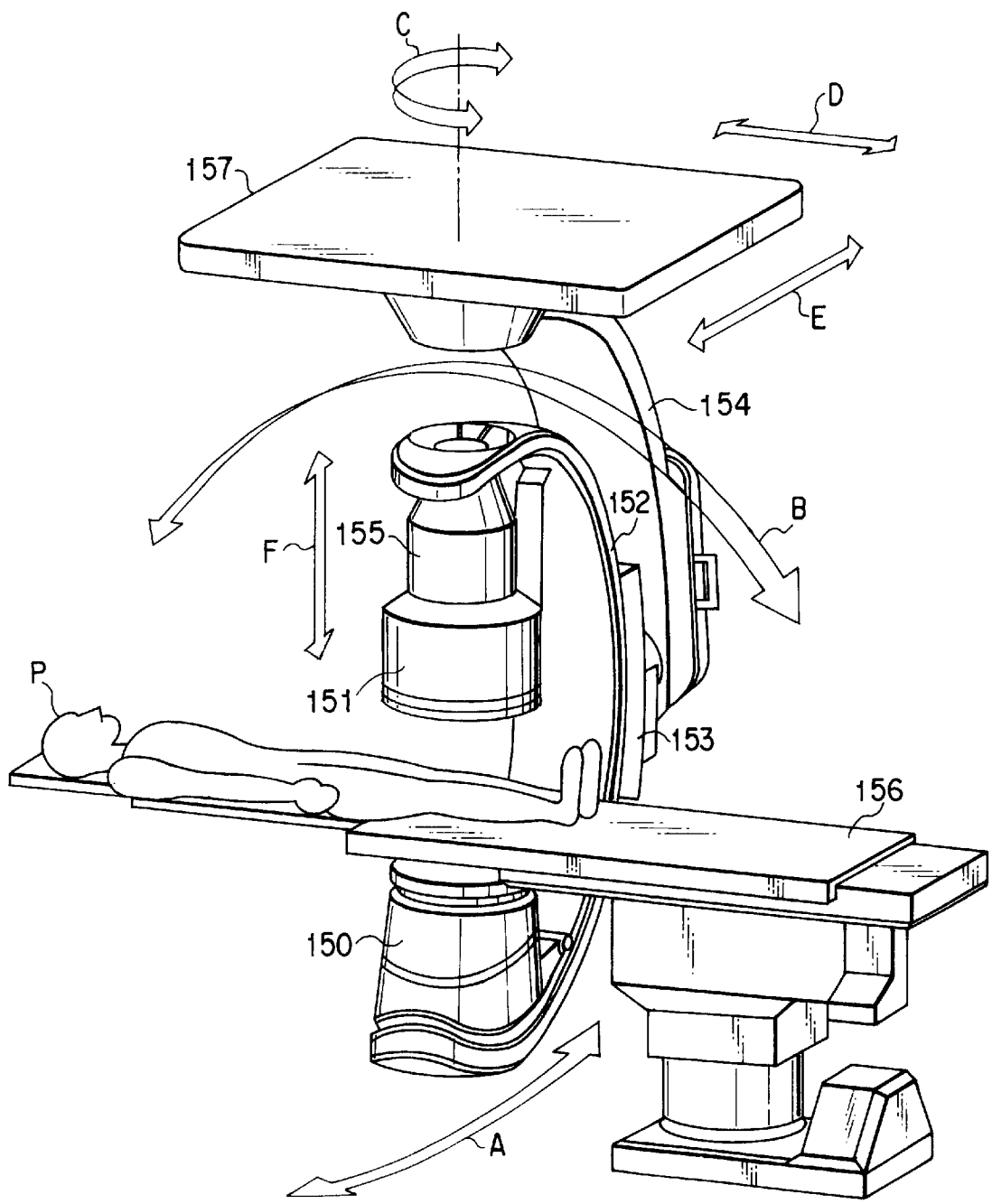
FIG. 1 is a perspective view of the gantry of a conventional circulatory system X-ray diagnostic apparatus.
Figure 3:
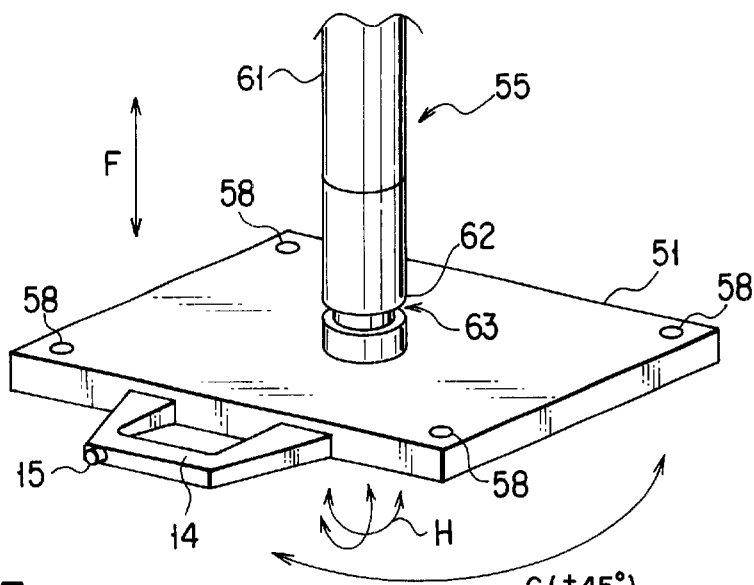
FIG. 3 is an enlarged view of the connecting portion of a suspension mechanism 55 and planar type X-ray detector 51 of FIG. 2.

FIG. 3 is an enlarged view of the connecting portion of the suspension mechanism 55 and planar type X-ray detector 51 of FIG. 1. The suspension mechanism 55 has a stretching/contracting mechanism, a rotating mechanism, and a tilt mechanism 63. The stretching/contracting mechanism moves the planar type X-ray detector 51 close to/away from the subject P (arrow F). The rotating mechanism rotates the planar type X-ray detector 51 about the central path of the X-rays (arrow G). The tilt mechanism 63 tilts the planar type X-ray detector 51 with respect to the central path of the X-rays (arrow H). In the stretching/contracting mechanism, an upper arm 61 is slidably inserted in a sheath pipe 60 mounted on the upper end of the C-shaped arm 52. In the rotating mechanism, a lower arm 62 is connected to the upper arm 61 to be axially rotatable.

A handle 14 is attached to the side surface of the planar type X-ray detector 51. With the handle 14, the planar type X-ray detector 51 can be manually moved conveniently. The handle 14 has a lock release switch 15. When the manual switch (lock release switch) 15 is pressed, all locks concerning motions (F, G, and H) of the planar type X-ray detector 51 are released, and the planar type X-ray detector 51 is free to move. Hence, the operator can move the planar type X-ray detector 51 freely.

Figure 4:
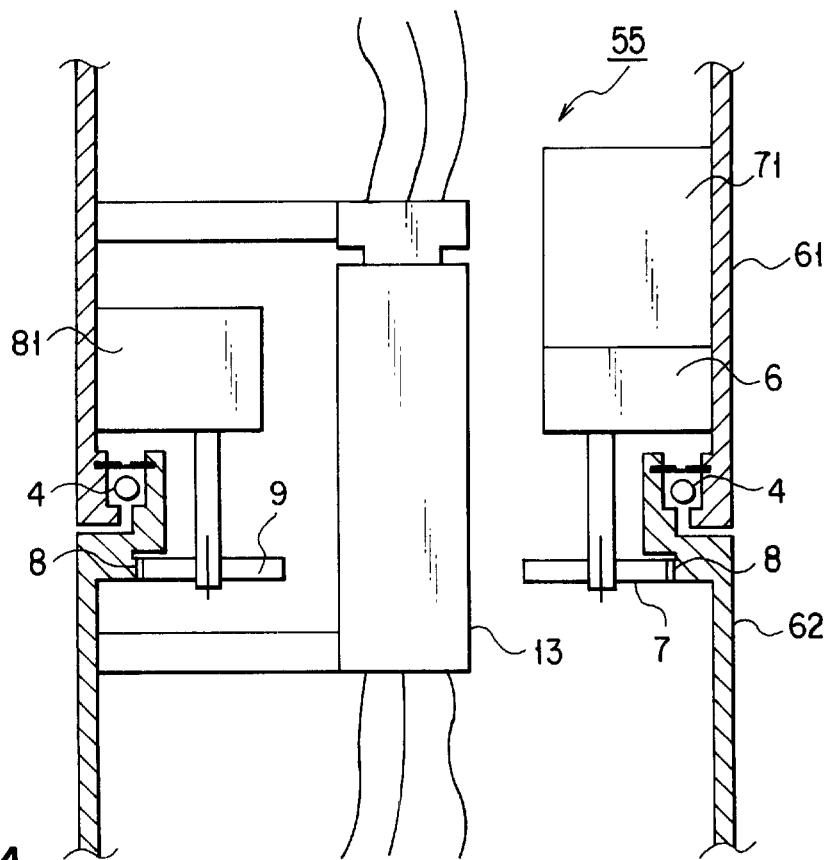
FIG. 4 is a view showing the internal structure of a rotating mechanism in the suspension mechanism 55 of FIG. 2.
Figure 5:
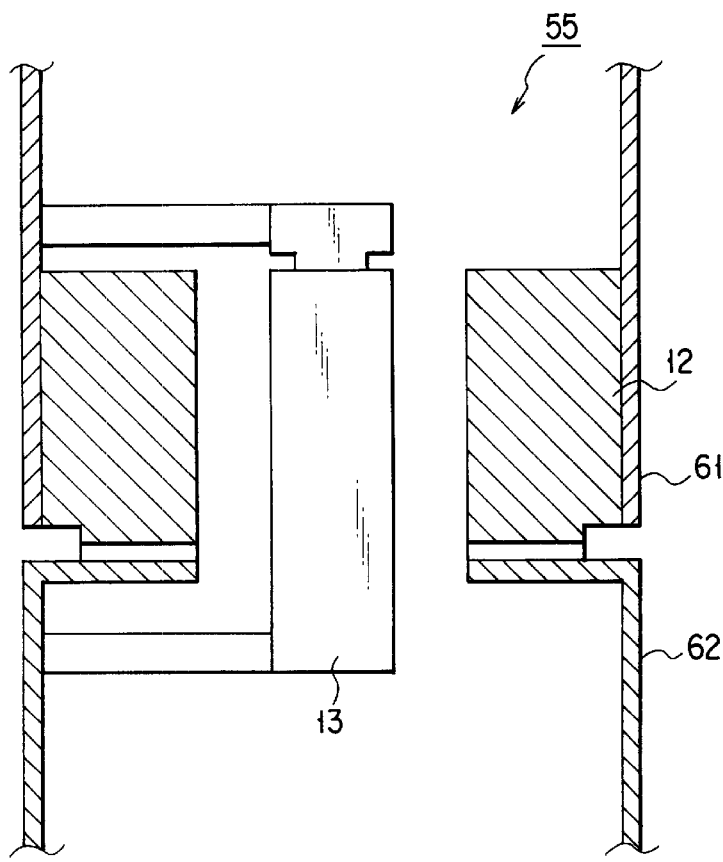
FIG. 5 is a view showing the internal structure of another rotating mechanism in the suspension mechanism 55 of FIG. 2.

FIG. 4 is a longitudinal sectional view of the connecting portion between the upper and lower arms 61 and 62. In the rotating mechanism, the upper and lower arms 61 and 62 are connected to each other through bearings 4. Rotation of the lower arm 62 with respect to the upper arm 61 is limited within a rotational range of ±45°. A sprocket 7 is connected to the driving shaft of an actuator 71, e.g., a motor, mounted on the inner wall of the upper arm 61 through a solenoid clutch 6. The sprocket 7 meshes with a gear 8 formed on the inner surface of the lower arm 62. A sprocket 9 meshes with the gear 8. The rotating shaft of a position sensor 81, e.g., a rotary encoder, is connected to the rotating shaft of the sprocket 9.

When the solenoid clutch 6 is disconnected, the lower arm 62 is free to rotate manually. When the solenoid clutch 6 is connected, rotation of the lower arm 62 is locked, and the lower arm 62 cannot be rotated manually. When the solenoid clutch 6 is connected and the actuator 71 is driven, the sprocket 7 rotates to axially rotate the lower arm 62. When the lower arm 62 rotates, the rotating shaft of the position sensor 81 rotates. Hence, the rotation angle of the lower arm 62 is detected. Exchange of electrical signals between the upper and lower arms 61 and 62 is realized by a slip ring 13, or a cable having such a sufficient length that it is not disconnected even when it is twisted by a rotation of ±45°. A hollow direct drive motor 12 incorporating a rotation holding bearing and a position sensor may be alternatively used as a driving source.

Figure 6:
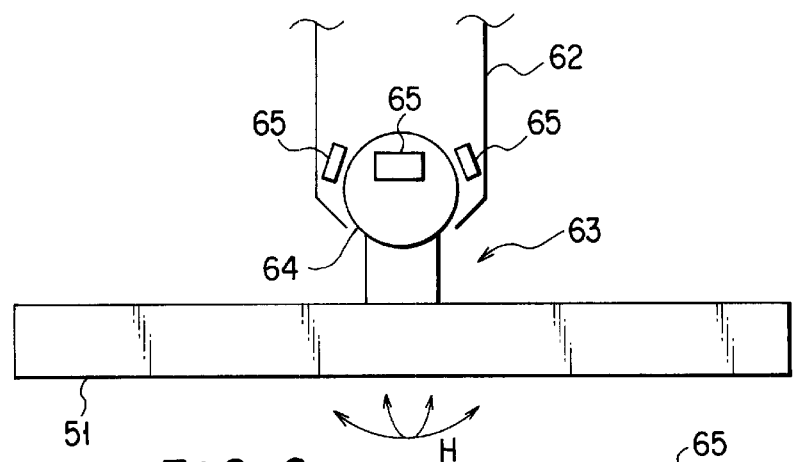
FIG. 6 is a view showing the internal structure of a tilt mechanism 63 in the suspension mechanism 55 of FIG. 3.
Figure 7:
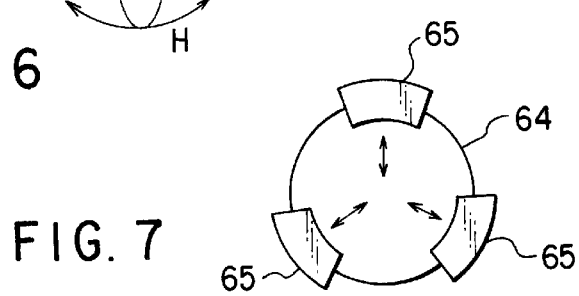
FIG. 7 is a plan view of a spheroidal rotor 64 and ultrasonic transducers 65 constituting the tilt mechanism 63 of FIG. 6.

FIGS. 6 and 7 show the internal structure of the tilt mechanism 63. As the actuator of the tilt mechanism 63, an ultrasonic motor is employed. The planar type X-ray detector 51 is connected to a spheroidal rotor 64 held at the lower end of the lower arm 62 in a free state. The planar type X-ray detector 51 can move freely about the rotor 64 as the center. Three ultrasonic transducers 65 are discretely arranged around the rotor 64. When the ultrasonic transducers 65 vibrate, they cause friction with the rotor 64, so as to rotate the rotor 64 in directions unique to the respective ultrasonic transducers 65. By combining the driving operation of the three ultrasonic transducers 65, the rotor 64 can be rotated in an arbitrary direction. When the rotor 64 rotates, the planar type X-ray detector 51 connected to it is tilted in a direction corresponding to the rotating direction of the rotor 64, by an angle corresponding to the rotation angle of the rotor 64, with respect to the central axis of the X-rays (arrow H).

Figure 8:
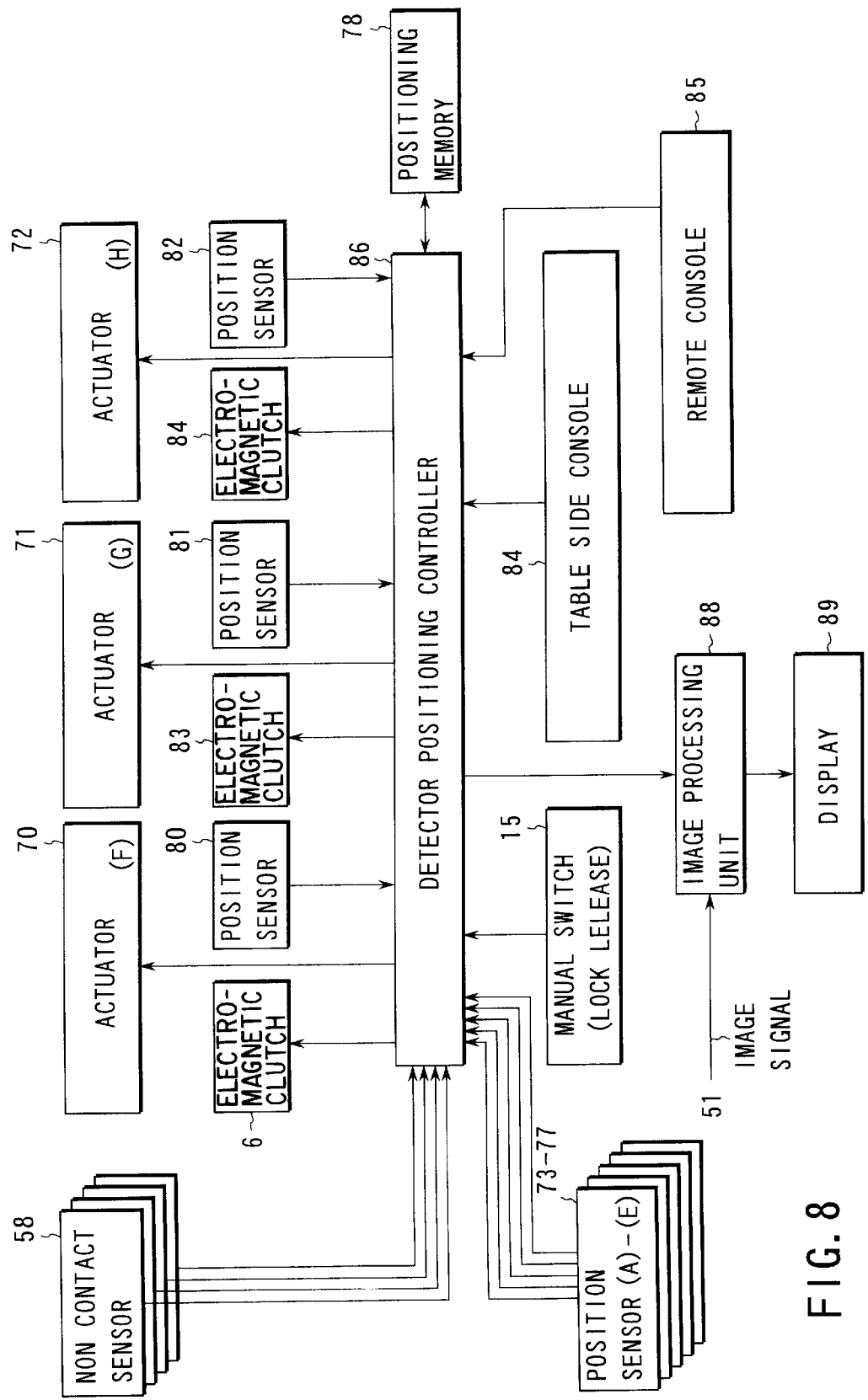
FIG. 8 is a block diagram showing the control system of the suspension mechanism 55 of FIG. 3.
Figure 9:
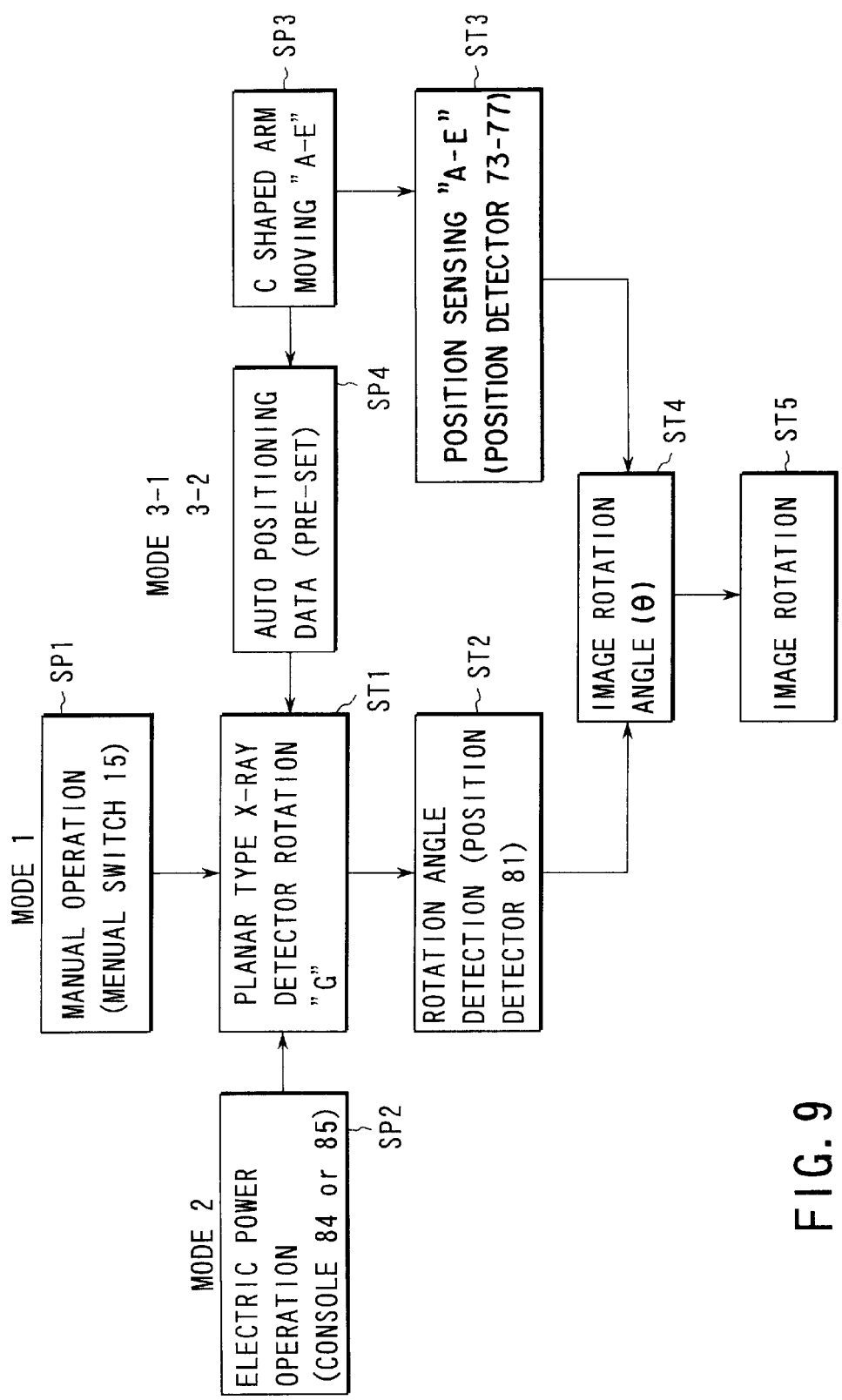
FIG. 9 is a view showing the procedure of the rotating operation of a planar type X-ray detector.

FIG. 8 shows the control system of the suspension mechanism 55 of FIG. 3. FIG. 9 shows the procedure of the rotating operation of the planar type X-ray detector 51. An actuator 70 is provided as a driving source to the stretching/contracting mechanism, in the same manner as in the actuator 71 of the rotating mechanism and an actuator 72 of the tilt mechanism. The tilt mechanism, the rotating mechanism, and the stretching/contracting mechanism are respectively provided with the solenoid clutch 6 and solenoid clutches 83 and 84 each serving also as a lock mechanism, and a position sensor 80, the position sensor 81, and a position sensor 82 for detecting the tilt angle, the rotation angle, and the slide amount. The operations of the actuators 70 to 72, and of the solenoid clutches 6, 83, and 84 are controlled by a detector positioning controller 86. The detector positioning controller 86 receives outputs from the position sensors 80, 81, and 82 as well as an output from the noncontact sensors 58 and outputs from position sensors 73 to 77 for detecting the tilt angle, the rotation angle, the slide amount, and the like of the C-shaped arm 52.

The detector positioning controller 86 also receives an output from the manual switch 15. When the manual switch 15 is pressed (SP1), the detector positioning controller 86 performs a control operation to disconnect the solenoid clutches 6, 83, and 84. Hence, all the locks concerning the motions (F, G, and H) of the planar type X-ray detector 51 are released. The planar type X-ray detector 51 is set free to move along the arrows F, G, and H, so that the operator can manually move it freely (mode 1). At this time, when the noncontact sensor 58 on either one of the four corners of the planar type X-ray detector 51 senses that this corner has moved close to the subject P by a predetermined distance or more, the detector positioning controller 86 connects the solenoid clutches 6, 83, and 84. This locks all motions of the planar type X-ray detector 51 to avoid any corner of the planar type X-ray detector 51 from abutting against the subject P. When all motions of the planar type X-ray detector 51 are locked, the actuators 70 to 72 may be controlled simultaneously to forcibly return the planar type X-ray detector 51.

The detector positioning controller 86 is connected to a table side console 84 for electric power operation (mode 2) and a remote console 85. Each of the table side console 84 and remote console 85 has three switches corresponding to the motions F, G, and H of the planar type X-ray detector 51. When the three switches of either the table side console 84 or remote console 85 are operated by the operator (SP2), the detector positioning controller 86 performs a control operation to drive the actuators 70 to 72, so that the planar type X-ray detector 51 performs an arbitrary one of the motions F, G, and H for an arbitrary amount with an electric power (ST1). At this time, when the noncontact sensor 58 at either one of the four corners of the planar type X-ray detector 51 detects that this corner has moved close to the subject P by a predetermined distance or more, the detector positioning controller 86 forcibly stops the driving operations of the actuators 70 to 72 to stop motion of the planar type X-ray detector 51. This avoids any corner of the planar type X-ray detector 51 from abutting against the subject P. Similarly, the actuators 70 to 72 may be controlled to forcibly return the planar type X-ray detector 51.

The detector positioning controller 86 is connected to an auto positioning memory 78. The positioning memory 78 stores two types of auto positioning data (SP4) individually related to the various postures (motions A to E) of the C-shaped arm 52 in advance. The first auto positioning data contains information concerning positions F to H of the planar type X-ray detector 51 to avoid any corner of the planar type X-ray detector 51 from abutting against the subject P when the C-shaped arm 52 is set in a certain posture. While the posture of the C-shaped arm 52 is being changed (SP3), the detector positioning controller 86 detects the posture of the C-shaped arm 52 from the position sensors 73 to 77 (ST3). The detector positioning controller 86 reads out the first positioning data related to the posture of the C-shaped arm 52 from the positioning memory 78, and controls the actuators 70 to 72 in accordance with the readout first auto positioning data. Thus, the planar type X-ray detector 51 is rotated appropriately (G), is tilted (H), and is slid (F) so that any of its corners automatically escapes from the subject P (modes 3–1).

The second auto positioning data contains information concerning the rotation angle of rotation (G) of the planar type X-ray detector 51 which is necessary for aligning the longitudinal direction of the subject P in an image imaged by the planar type X-ray detector 51 with the vertical direction of the image of a display 89 when the C-shaped arm 52 is set in a certain posture. While the posture of the C-shaped arm 52 is being changed (SP3), the detector positioning controller 86 detects the posture of the C-shaped arm 52 from the position sensors 73 to 77 (ST3). The detector positioning controller 86 reads the second positioning data related to the posture of the C-shaped arm 52 out of the positioning memory 78, and controls the actuator 71 in accordance with the readout second auto positioning data. Thus, the planar type X-ray detector 51 is rotated appropriately (G), and an image obtained by the planar type X-ray detector 51 is displayed on the display 89 with the longitudinal direction of its subject P being aligned with the vertical direction of the screen of the display 89 (modes 3–2).

The above four modes can be arbitrarily selected by operating the corresponding switches of the consoles 84 and 85.

The function of aligning the longitudinal direction of the subject P in the image with the vertical direction of the screen of the display 89 can be realized not only by rotation of the planar type X-ray detector 51 but also by image processing (image rotation). This image processing will be described below.

Figure 10:
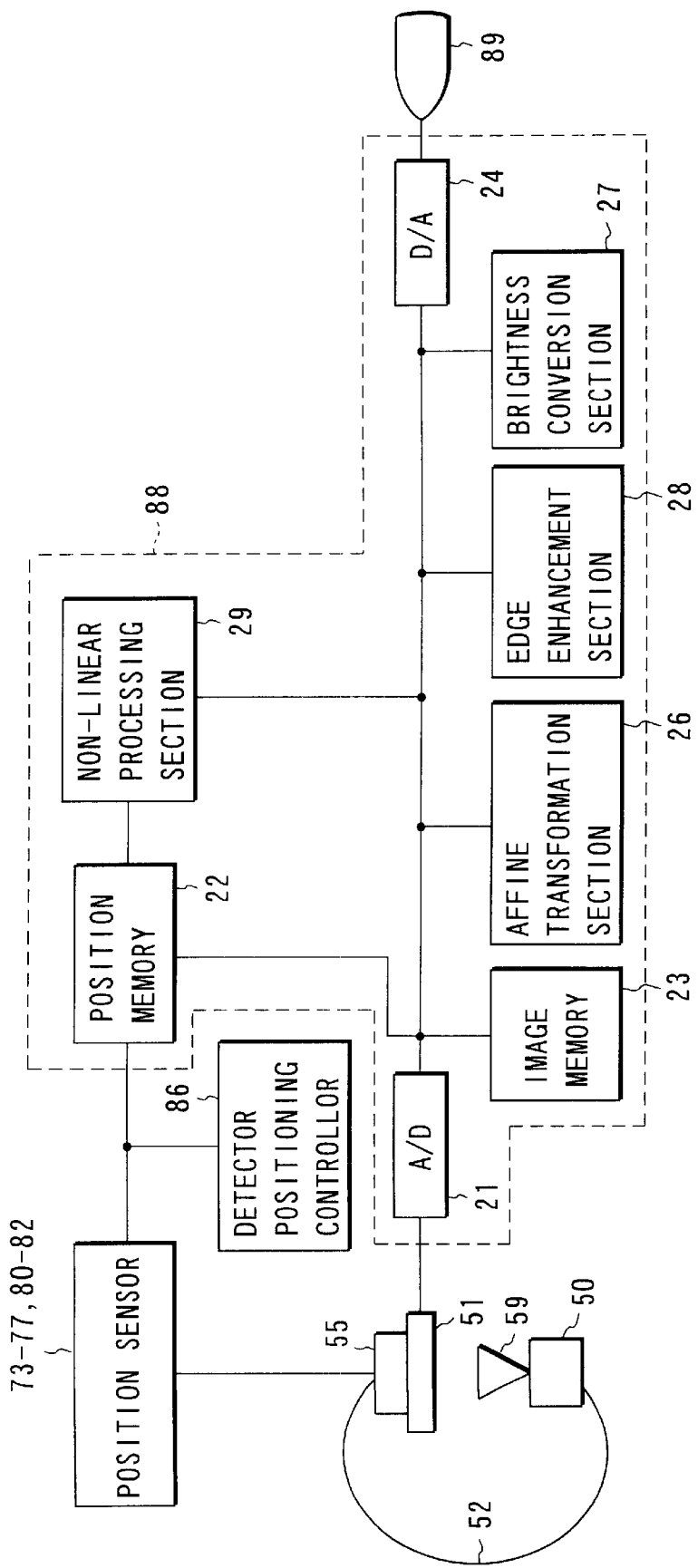
FIG. 10 is a block diagram of the image processing unit of FIG. 8.

FIG. 10 is a block diagram of an image processing unit 88 of FIG. 8. The image processing unit 88 receives an image signal from the planar type X-ray detector 51. The image processing unit 88 has an A/D converter 21, D/A converter 24, image memory 23, a position memory 22, affine transformation section 26, brightness conversion section 27, edge enhancement section 28, and nonlinear processing section 29. The A/D converter 21 converts the image signal into a digital signal. The D/A converter 24 converts the processed image into an analog signal. The image memory 23 stores image data. The position memory 22 stores posture data of the C-shaped arm 52 supplied from the detector positioning controller 86 and the posture data of the planar type X-ray detector 51. The affine transformation section 26 transforms the image by affine transformation such as enlargement, reduction, and rotation. The brightness conversion section 27 converts the brightness of the image. The edge enhancement section 28 enhances the outline of an internal organ or the like in the image. The nonlinear processing section 29 corrects distortion of the image. The position memory 22 also stores the patient's name, the patient's ID number, the date of imaging, and the imaging conditions such as the imaging mode (the size of the field of view of the detector), the tube voltage, the tube current, and the pulse width.

Figure 11:
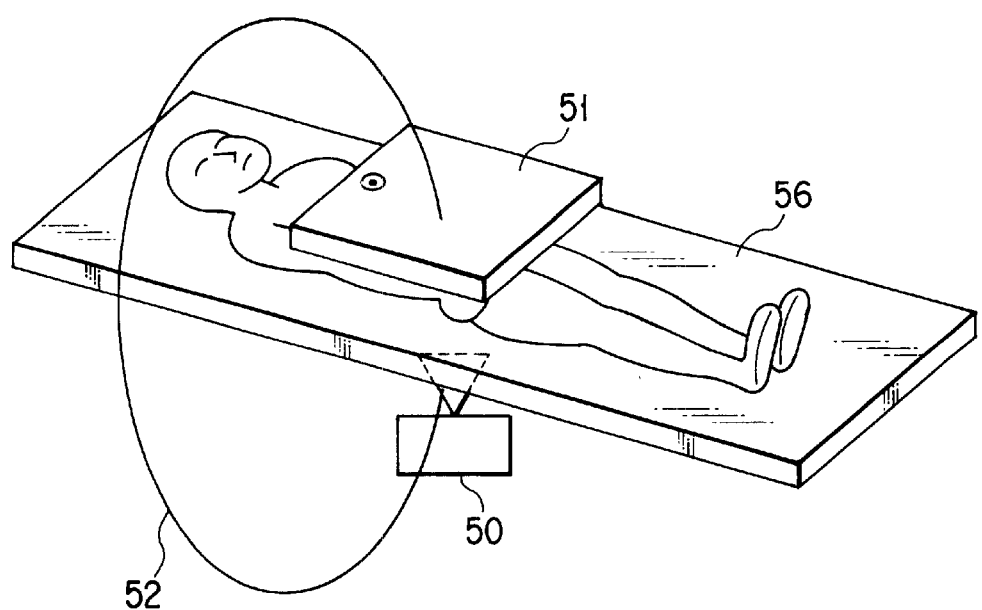
FIG. 11 is a perspective view showing a side approach of this embodiment.
Figure 12:
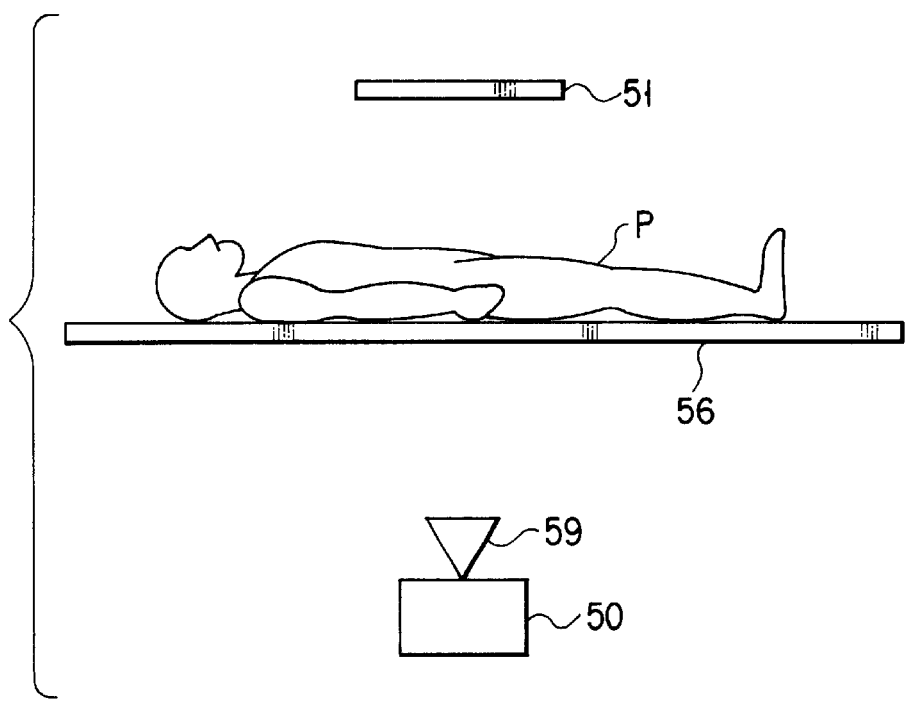
FIG. 12 is a side view of FIG. 11.
Figure 13:
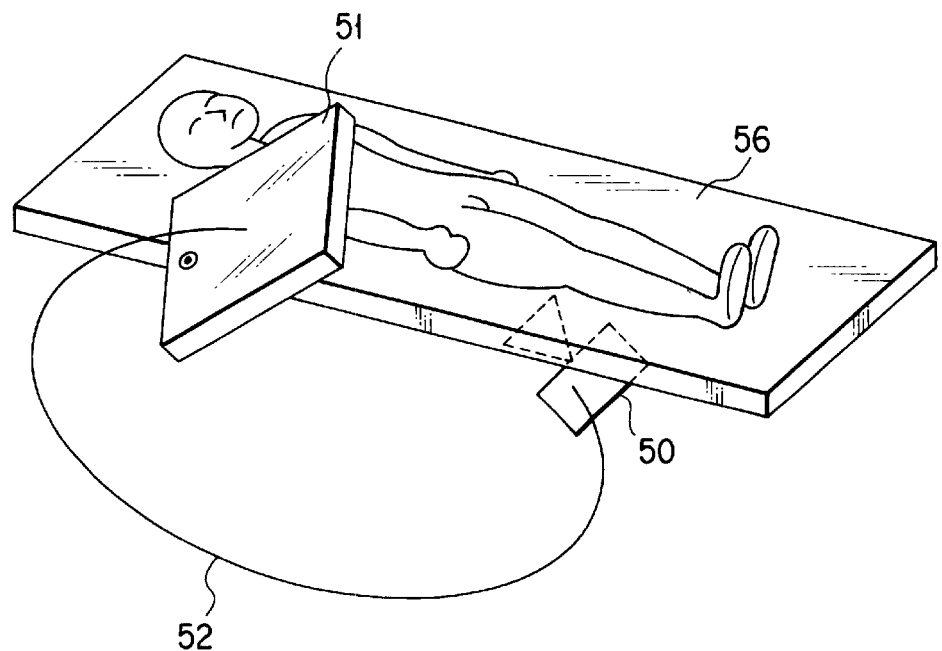
FIG. 13 is a perspective view showing a side approach accompanying a tilt of this embodiment.

Assume that, when the arm 52 is set in a side approach state with respect to the subject P, the longitudinal direction of the subject P on the image is aligned with the vertical direction of the display 89, as shown in FIGS. 11 and 12. This state is defined as the reference.

From this reference state, when the C-shaped arm 52 is rotated through 45° (arrow C) and is tilted by 45° (arrow B), the longitudinal direction of the subject P on the image is undesirably tilted from the vertical direction of the display 89 by 45° in response to the rotation C of the C-shaped arm 52. At this time, the affine transformation section 26 performs image processing corresponding to a motion of inversely rotating it through substantially 45° with respect to the rotation angle of 45° of the rotation C of the C-shaped arm 52 (ST4 and ST5 of FIG. 9). Hence, the longitudinal direction of the subject P on the image is aligned with the vertical direction of the display 89.

A general equation of this affine processing is:

$$\begin{bmatrix} X \\ Y \end{bmatrix} = \begin{bmatrix} A & B \\ C & D \end{bmatrix} \begin{bmatrix} x \\ y \end{bmatrix} + \begin{bmatrix} E \\ F \end{bmatrix} \quad (1)$$

Note that (x, y) represents coordinates before conversion, (X, Y) represents coordinates after conversion, A, B, C, and D are conversion coefficients concerning rotation (enlargement or reduction), and E and F are conversion coefficients with which translational motion is performed. Transformation of equation (1) to apply it to a case wherein the image is rotated by a rotation angle θ yields:

$$\begin{bmatrix} X \\ Y \end{bmatrix} = \begin{bmatrix} A & B \\ C & D \end{bmatrix} \begin{bmatrix} \cos\theta & -\sin\theta \\ \sin\theta & \cos\theta \end{bmatrix} \begin{bmatrix} x \\ y \end{bmatrix} + \begin{bmatrix} E \\ F \end{bmatrix} \quad (2)$$

$$= \begin{bmatrix} A' & B' \\ C' & D' \end{bmatrix} \begin{bmatrix} x \\ y \end{bmatrix} + \begin{bmatrix} E \\ F \end{bmatrix}$$

Figure 14:
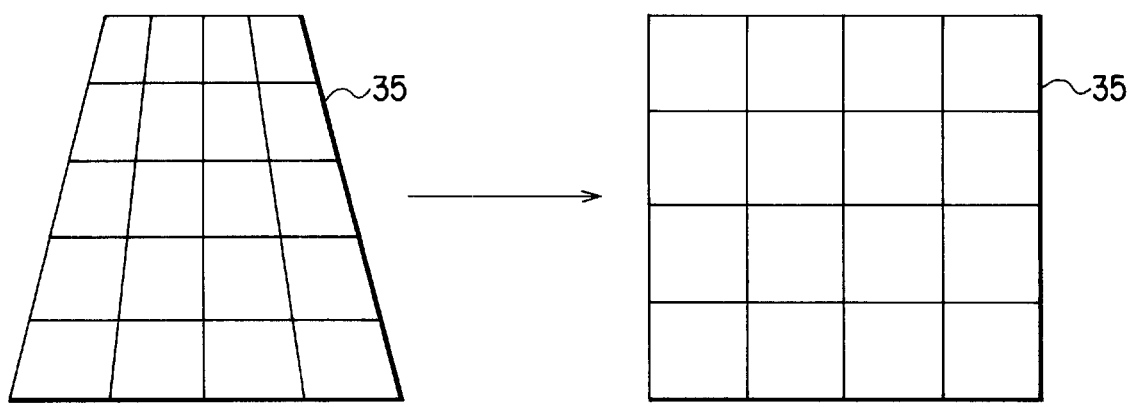
FIG. 14 is a view showing distortion correction done by the affine transformation section 26 of FIG. 10.

When the planar type X-ray detector 51 is tilted, the X-ray enlargement ratio becomes nonuniform within the detection plane of the planar type X-ray detector 51 in accordance with a change in distance from the focal point of the X-ray tube 50. Therefore, the image distorts as shown in the left side of FIG. 14. In this case, as shown in the right side of FIG. 14, in order to solve this distortion, the nonlinear processing section 29 subjects the image to a nonlinear process to set the X-ray enlargement ratio constant on the basis of the direction of tilt and the tilt angle of the planar type X-ray detector 51.

The flow of the inspection process with the arrangement of this embodiment will be described. The operator sets the arm 52 in such a position and direction that the target portion of the subject P can be observed easily. This posture is output from the position sensors 73 to 77. The detector positioning controller 86 rotates the planar type X-ray detector 51 in accordance with the second auto positioning data related to the posture read from the position sensors 73 to 77. In this rotation, when rotation of the planar type X-ray detector 51 is stopped midway in accordance with the outputs from the noncontact sensors 58, a message indicating that rotation of the planar type X-ray detector 51 does not reach the rotation angle represented by the second auto positioning data is displayed. Upon reception of this message, the operator manually and additionally rotates adds rotation of the planar type X-ray detector 51. When rotation of the planar type X-ray detector 51 reaches the rotation angle represented by the second auto positioning data, this fact is displayed.

After the postures of the C-shaped arm 52 and planar type X-ray detector 51 are set in this manner, imaging is performed with the preset X-ray conditions. The obtained image is converted by the A/D converter 21 into digital signals. The converted image data is distortion-corrected by the nonlinear processing section 29, and is stored once in the image memory 23 comprising a hard disk and RAID. An image distortion is corrected on the basis of the rotation angle of the planar type X-ray detector 51 obtained from the imaging condition memory 22. The corrected image is subjected to affine transformation by the affine transformation section 26, edge enhancement transformation by the edge enhancement section 28, density (density gradation) conversion by the brightness conversion section 27, and the like, if necessary, is then converted into analog signals by the D/A converter 24, and the image is displayed on the display 89.

Figure 15:
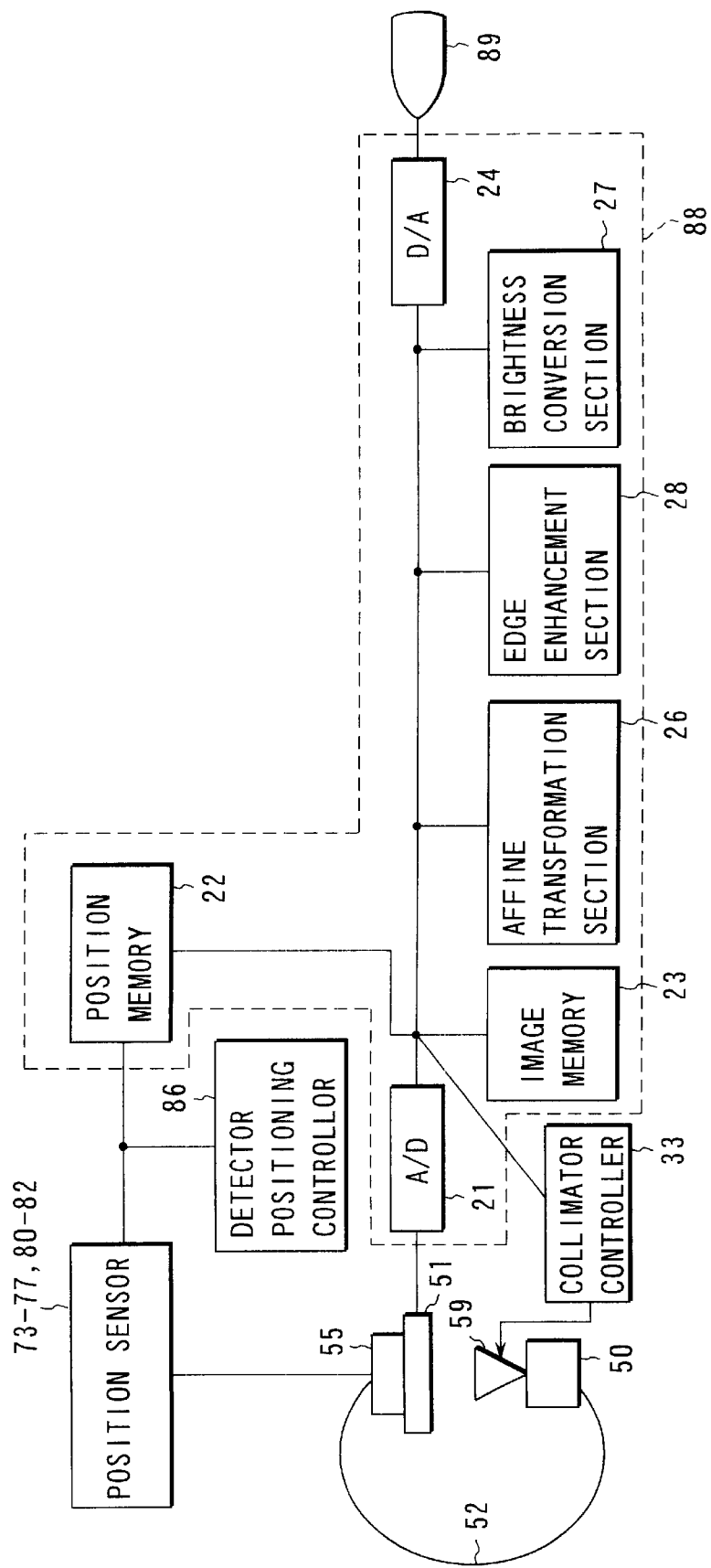
FIG. 15 is a block diagram showing a collimator controller 33 of this embodiment.
Figure 16:
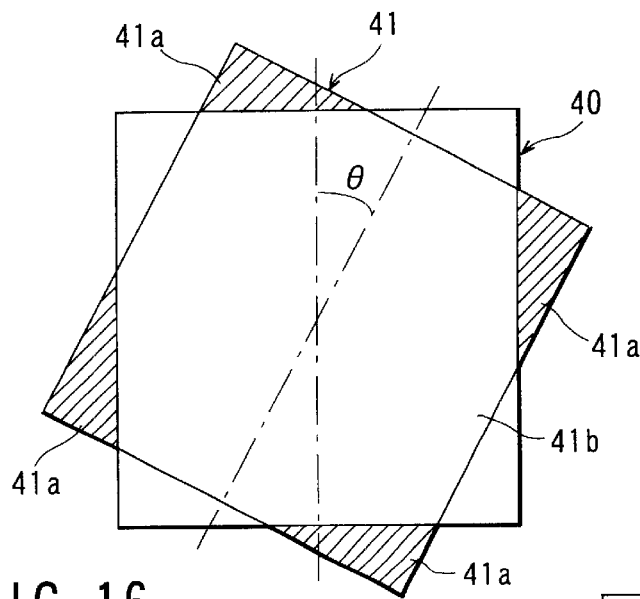
FIG. 16 is a view showing the display region of a display from which images subjected to rotation by the affine transformation section 26 of FIG. 10 are removed.

As described above, when the image is rotated such that the longitudinal direction of the subject P on the image is aligned with the vertical direction of the display 89, portions 41a of the image extend outside a display region 40, as shown in FIG. 16. These excluded portions 41a are not displayed, and only a central portion 41b other than the excluded portions 41a is displayed. X-rays corresponding to the portions 41a cause unnecessary exposure. In order to shield these portions, a collimator controller 33 in FIG. 15 controls a collimator 59 to form an aperture in it.

The flow of inspection process with this arrangement will be described. The operator sets the arm 52 in such a posture that the target portion can be observed easily. The preset posture is detected by the position sensors 73 to 77. The detector positioning controller 86 rotates the planar type X-ray detector 51 on the basis of the detected posture. When the longitudinal direction of the subject P and the vertical direction of the display are misaligned from C each other due to this rotation, the image is rotated. In this case, the rotation angle θ through which the image is rotated in this image processing is stored. The collimator controller 33 changes the shape of the aperture of the collimator 59 so that regions corresponding to the portions 41a excluded from the display region 40 are not irradiated with the X-rays.

Figure 17:
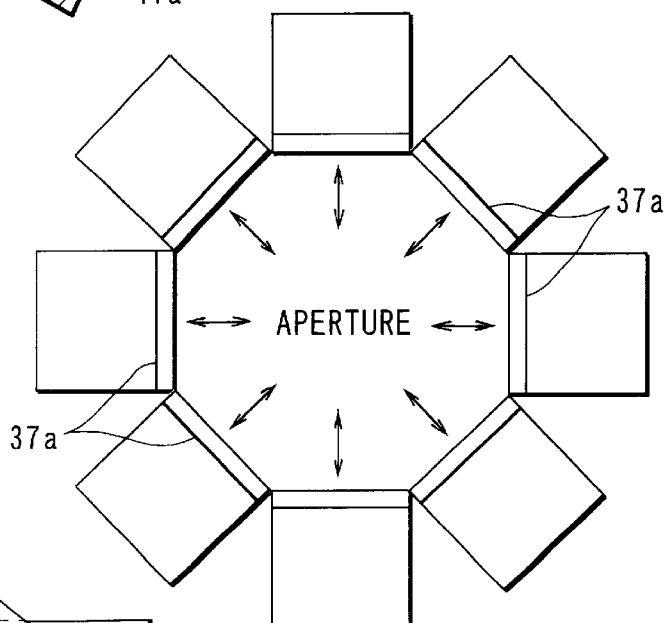
FIG. 17 is a plan view of the collimator plates of the collimator 59 of FIG. 15.
Figure 18:
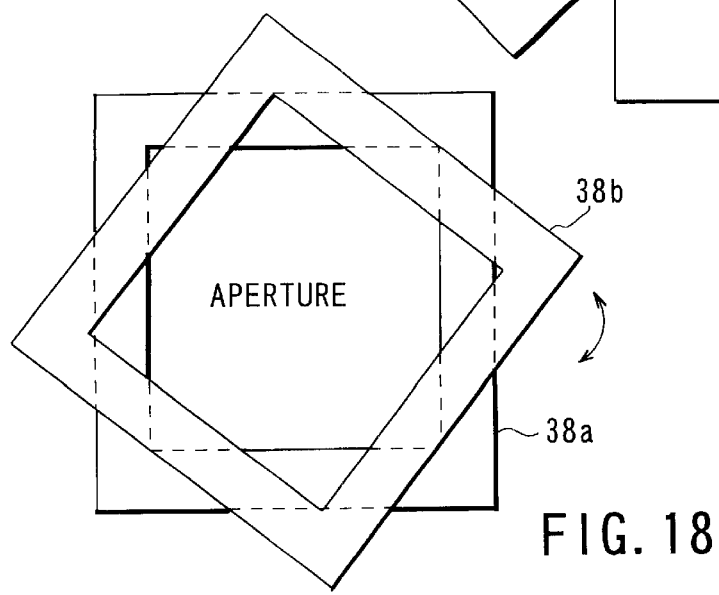
FIG. 18 is a plan view of other collimator plates of the collimator 59 of FIG. 15.

FIG. 17 shows the arrangement of the collimator plates of the collimator 59. In the collimator 59, a plurality of collimator plates 37a are provided to be radially movable about the X-ray axis as the center. In the case of FIG. 17, a total of eight collimator plates 37a are provided. When the image is rotated by image processing, the collimator controller 33 moves the respective collimator plates 37a on the basis of the rotation angle θ to shield portions corresponding to the portions 41a that are not displayed. This avoids unnecessary exposure. The collimator 59 may be formed by combining hollow square collimator plates 38a and 38b, as shown in FIG. 18. The collimator controller 33 rotates only one collimator plate 38b in the same direction and through the same angle as in rotation of the rotation angle θ done by image processing.

Figure 19:
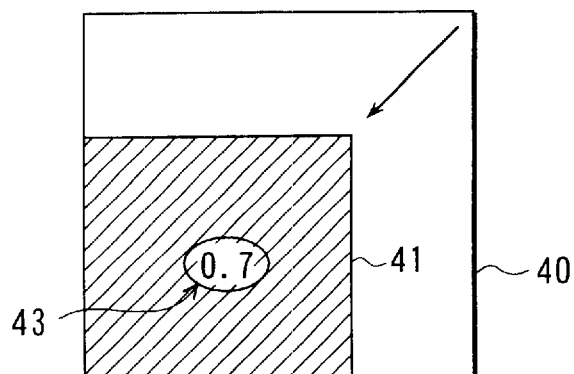
FIG. 19 is a view showing a case wherein a reduction ratio concerning reduction performed by the affine transformation section 26 of FIG. 10 is numerically expressed.
Figure 20:
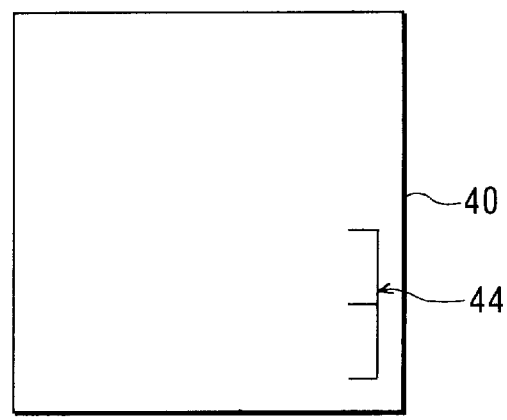
FIG. 20 is a view showing a case wherein the reduction ratio of FIG. 19 is expressed by a scale.
Figure 21:
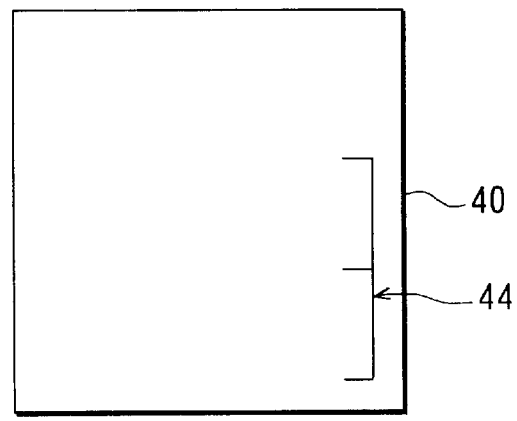
FIG. 21 is a view showing enlargement of the scale of FIG. 20 that accompanies a change in reduction ratio.

To eliminate the portions 41a that are not displayed, when the image is rotated, it is sometimes reduced simultaneously. In this case, the degree of reduction is displayed in character or numeric indication 43 as a reduction ratio index on the display region 40, as shown in FIG. 19, so that it can be recognized easily. Alternatively, as shown in FIGS. 20 and 21, a scale bar 44 indicating the reference length of the reduction ratio index is displayed simultaneously. The scale bar 44 stretches or contracts in accordance with the reduction ratio. Alternatively, the image may not be reduced or the display region may not be enlarged in this manner, but a scroll bar (not shown) may be displayed on the display region 40, and the image itself may be moved such that portions excluded from the display region 40 can be seen.

Figure 22:
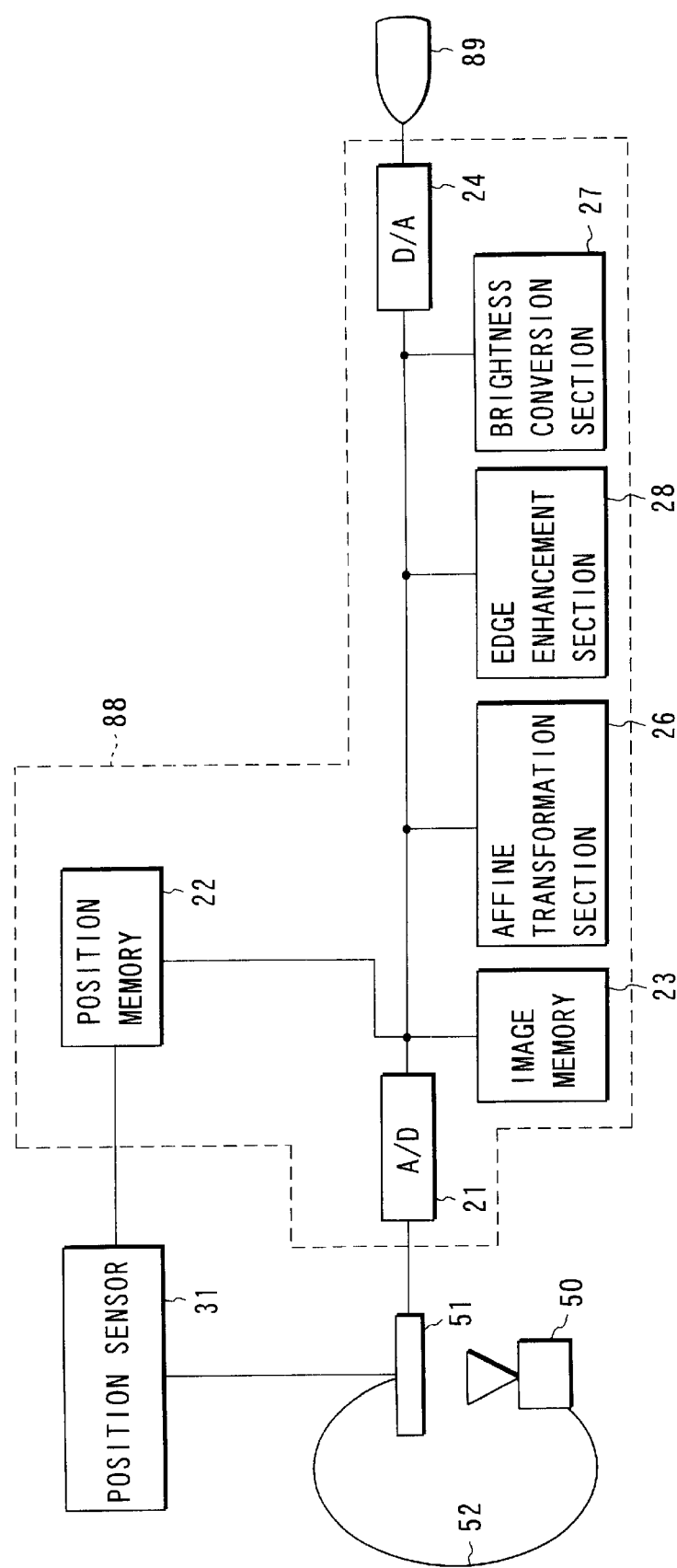
FIG. 22 is a block diagram showing a case of this embodiment wherein an image is rotated with respect to the display region of the display by only image processing.

If only the longitudinal direction of the subject P in the image need be aligned with the vertical direction of the screen, a simple arrangement as shown in FIG. 22 suffices.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
   an X-ray tube configured to irradiate a subject with X-rays;
   a rectangular planar type X-ray detector formed by arraying a plurality of solid-state detection elements;
   a supporting mechanism configured to support said X-ray tube and said planar type X-ray detector in arbitrary postures with respect to the subject;
   a suspending mechanism configured to suspend said planar type X-ray detector from said supporting mechanism, said suspending mechanism including a rotating mechanism for rotating said planar type X-ray detector through an arbitrary angle about a central path of the X-rays, said rotating mechanism including an actuator configured to drive said planar type X-ray detector to rotate;
   a posture detector configured to detect postures of said X-ray tube and said planar type X-ray detector with respect to the subject; and
   a controller configured to control said actuator such that a corner of said planar type X-ray detector does not abut against the subject, thereby rotating said planar type X-ray detector through an angle corresponding to the detected posture.

2. An apparatus according to claim 1, wherein said suspending mechanism has a tilt mechanism configured to tilt said planar type X-ray detector through an arbitrary angle with respect to the central path of the X-rays.

3. An apparatus according to claim 2, further comprising a detector configured to detect a tilt angle of said planar type X-ray detector with respect to the central axis of the X-rays, and an image processing unit configured to correct a distortion in an image obtained by said planar type X-ray detector on the basis of the detected tilt angle in accordance with nonlinear transformation.

4. An apparatus according to claim 1, wherein said suspending mechanism has a mechanism configured to move said planar type X-ray detector close to/away from the subject.

5. An apparatus according to claim 1, wherein said rotating mechanism has locking mechanism configured to lock rotation of said planar type X-ray detector.

6. An apparatus according to claim 5, further comprising a lock release switch provided to a handle of said planar type X-ray detector.

7. An apparatus according to claim 1, further comprising an operation switch configured to operate rotation of said-planar type X-ray detector with said actuator.

8. An apparatus according to claim 1, wherein said controller controls said actuator such that a longitudinal direction of the subject on an image obtained by said planar type X-ray detector and a vertical direction of an image display screen substantially coincide with each other, thereby rotating said planar type X-ray detector through an angle corresponding to the detected posture.

9. An apparatus according to claim 8, further comprising a clutch disconnecting switch provided to a handle of said planar type X-ray detector.

10. An apparatus according to claim 1, further comprising a clutch function connected to a driving shaft of said actuator.

11. An apparatus according to claim 1, further comprising an image processing unit configured to rotate an image obtained by said planar type X-ray detector on the basis of the detected posture such that a longitudinal direction of the subject on the image and a vertical direction of an image display screen substantially coincide with each other.

12. An apparatus according to claim 1, further comprising an image processing unit configured to rotate an image obtained by said planar type X-ray detector on the basis of the detected posture.

13. An apparatus according to claim 1, further comprising an image processing unit configured to reduce an image obtained by said planar type X-ray detector or enlarging an image display region of a display screen, when the image extends outside said image display region, so that the image is displayed within said image display region.

14. An apparatus according to claim 13, wherein said image processing unit has a function of displaying a reduction ratio of the image or an index indicating the reduction ratio.

15. An apparatus according to claim 1, further comprising a plurality of noncontact or contact sensors provided to or near corners of said planar type X-ray detector, and mechanism configured to limit rotation of said planar type X-ray detector on the basis of outputs from said proximity sensors.

16. An apparatus according to claim 1, wherein said suspending mechanism includes a tilt mechanism for tilting said planar type X-ray detector by an arbitrary angle about a central path of the X-rays.

17. An apparatus according to claim 1, wherein said suspending mechanism includes a mechanism for moving said planar type X-ray detector close to/away from the subject.

18. An apparatus according to claim 1, further comprising:
   a collimator unit provided between said X-ray tube and the subject, and a controller configured to control said collimator unit, when part of an image obtained by said planar type X-ray detector extends outside an image display region of a display screen, to shield a region corresponding to the part of the image extending outside said image display region.

* * * * *